US010175934B2

(12) United States Patent
Amadu

(10) Patent No.: US 10,175,934 B2
(45) Date of Patent: Jan. 8, 2019

(54) SYSTEM FOR OPTIMIZATION OF MUSIC LISTENING

(71) Applicant: ARKAMYS, Paris (FR)

(72) Inventor: Frédéric Amadu, Chelles (FR)

(73) Assignee: ARKAMYS, Paris (FR)

( * ) Notice: Subject to any disclaimer, the term of this patent is extended or adjusted under 35 U.S.C. 154(b) by 0 days.

(21) Appl. No.: 15/108,567

(22) PCT Filed: Dec. 19, 2014

(86) PCT No.: PCT/EP2014/078874
§ 371 (c)(1),
(2) Date: Jun. 27, 2016

(87) PCT Pub. No.: WO2015/101534
PCT Pub. Date: Jul. 9, 2015

(65) Prior Publication Data
US 2016/0321030 A1    Nov. 3, 2016

(30) Foreign Application Priority Data
Dec. 30, 2013  (FR) .................................. 13 63670

(51) Int. Cl.
*G06F 3/16*    (2006.01)
*H04R 27/00*    (2006.01)
(Continued)

(52) U.S. Cl.
CPC .............. *G06F 3/165* (2013.01); *A61B 5/125* (2013.01); *G06F 3/162* (2013.01); *H04L 65/602* (2013.01);
(Continued)

(58) Field of Classification Search
CPC . G06F 3/165; G06F 3/16; H04L 67/22; H04L 65/4084; H04L 65/1059;
(Continued)

(56) References Cited

U.S. PATENT DOCUMENTS

2002/0068986 A1 * 6/2002 Mouline ................ A61B 5/121
   700/94
2003/0128859 A1   7/2003  Greene et al.
(Continued)

FOREIGN PATENT DOCUMENTS

WO         01/24576 A1    4/2001
WO     WO 01/24576 A1 *   4/2001

*Primary Examiner* — Yogeshkumar Patel
(74) *Attorney, Agent, or Firm* — IM IP Law; C. Andrew Im; Chai Im

(57) ABSTRACT

A system for optimizing music listening which includes a multimedia server controlled by a user. The multimedia server includes a transmitter of the multimedia server to transmit an audio stream to various connected appliances provided with an acoustic emitter and a selector to select at least one connected appliance to which the audio stream is transmitted. A predetermined table of characteristics links the various connected appliances to a measurement of the acoustic reproduction capabilities thereof. A predetermined user table links at least one user with the hearing capabilities thereof. An adapter to adapt the audio stream in accordance with the measurement of the acoustic reproduction capabilities of the connected appliance to which the audio stream is transmitted and in accordance with the hearing capabilities of the user connected to the multimedia server.

7 Claims, 2 Drawing Sheets

(51) Int. Cl.
*H04R 3/12* (2006.01)
*A61B 5/12* (2006.01)
*H04L 29/08* (2006.01)
*H04L 29/06* (2006.01)
*H04R 27/02* (2006.01)

(52) U.S. Cl.
CPC ............ *H04L 67/306* (2013.01); *H04R 3/12* (2013.01); *H04R 27/00* (2013.01); *H04R 27/02* (2013.01); *H04R 2205/041* (2013.01); *H04R 2499/13* (2013.01)

(58) Field of Classification Search
CPC . H04L 65/4092; H04L 65/602; H04L 65/604; H04L 67/02; H04L 67/141; H04L 67/20; H04R 27/00; H04R 3/00; H04R 2227/003
USPC .................................... 381/97, 198, 102, 82
See application file for complete search history.

(56) References Cited

U.S. PATENT DOCUMENTS

| | | | | |
|---|---|---|---|---|
| 2014/0050334 A1* | 2/2014 | Antonellis | ............ | H03G 5/005 381/97 |
| 2014/0298195 A1* | 10/2014 | Chatterjee | ............ | H04L 67/306 715/745 |

* cited by examiner

SYSTEM FOR OPTIMIZATION OF MUSIC LISTENING

RELATED APPLICATIONS

This application is a § 371 application from PCT/EP2014/078874 filed Dec. 19, 2014, which claims priority from French Patent Application No. 13 63670 filed Dec. 30, 2013, each of which is incorporated herein by reference in its entirety.

FIELD OF THE INVENTION

The present invention relates to a music listening optimization system destined for several appliances connected to a multimedia server. The invention relates to all connected appliances able to emit an audio stream originating from a network and, more particularly, appliances connected to the Internet such as SmartPhones, connected car radios of motor vehicles, connected touch tablets and televisions.

The invention relates to the field of telecommunications and more particularly Internet-access electronic equipment which performs the emission of audio content from a multimedia server.

BACKGROUND OF THE INVENTION

There are numerous Internet-based platforms which make it possible to transmit a music stream to a connected terminal provided with acoustic emission means. For example, in the case of a motor vehicle car radio, the audio stream is streamed to the car radio which transforms the audio signal so as to emit it on the vehicle's various loudspeakers. The music stream is stored in a so-called "Cloud". The car radio can comprise a modulatable amplification system allowing the user to modify the parameters of the audio signal at his convenience. However, it is often very complex to effectively adjust the various parameters of the car radio and these parameters may vary as a function of the audio stream and of the listener's wishes.

Moreover, reproduction qualities vary greatly between two types of terminals, for example between a Smartphone possessing a simple loudspeaker operating on a single audio channel and an audio system possessing a Home Cinema device. It is thus particularly difficult to adjust all the connected equipment in the same manner so as to emit an audio stream at one's convenience.

Furthermore, there are also technologies which make it possible, from a connected terminal, to redirect an audio stream to another terminal. For example, the "Air Play" (registered trademark) technology makes it possible to use a touch tablet to broadcast a stream from the touch tablet on a connected television.

These technologies are available through a domestic network, conventionally of Wifi ("Wireless Fidelity") type, but do not make it possible to interact with appliances connected on a network external to the domestic network. These technologies are therefore not adapted for controlling the audio stream on board a motor vehicle.

OBJECT AND SUMMARY OF THE INVENTION

The present invention aims to remedy these drawbacks by proposing a music listening optimization system aimed at controlling all types of connected appliances which are able to emit an audio stream.

For this purpose, the invention relates to a music listening optimization system comprising a multimedia server controlled by a user, said multimedia server comprising means for transmitting an audio stream on different connected appliances provided with acoustic emission means, means for selecting at least one connected appliance to which said audio stream is transmitted, a predetermined table of characteristics linking said various connected appliances with a measure of their acoustic reproduction capabilities, a predetermined user table linking at least one user with his hearing capabilities, and means for adapting said audio stream as a function of the measure of the acoustic reproduction capabilities of the connected appliance to which said audio stream is transmitted and as a function of the hearing capabilities of the user connected to said multimedia server.

The invention thus makes it possible to control all types of connected appliances which are able to emit an audio stream by adapting the audio stream at one and the same time to the appliance on which the audio stream is emitted and by adapting the audio stream to the user according to his hearing capabilities. The reproduction of the sound experienced by a given user is thus greatly improved with respect to existing devices. As a variant, the reproduction of the sound can also be adapted as a function of the user's preferences. For example, when the audio stream emits music whose rhythmic base is calm, the user may prefer to enhance listening in respect of high-pitched sounds.

According to one embodiment, said multimedia server also comprises means for transmitting a video stream associated with said audio stream. This embodiment makes it possible to associate a video stream with the audio stream. As a variant, the video stream can comprise processings adapted to the appliance on which the video stream is transmitted and/or processings associated with the user's preferences or capabilities.

According to one embodiment, said multimedia server comprises a control interface usable from at least one of the various connected appliances, the control interface being able to advise as regards the connected user. This embodiment makes it possible at one and the same time to identify the user and to control all the simultaneously connected appliances.

According to one embodiment, said predetermined table of characteristics is filled in during a step of installing a connected appliance as a function of the response of the acoustic emission means to various stimuli. This embodiment makes it possible to ascertain the reproduction characteristics of the connected appliance very rapidly by using a microphone and by analyzing the sound reproduced and recorded. As a variant, the predetermined table of characteristics can comprise several behaviors as a function of ambient noise level.

According to one embodiment, the means for adapting the audio stream comprise several filters of IIR type connected in series whose characteristics are tailored as a function of the measure of the acoustic reproduction capabilities of the connected appliance to which said audio stream is transmitted.

According to one embodiment, said predetermined user table is filled in during a step of defining the hearing capabilities of a user at several predetermined characteristic frequencies. This embodiment makes it possible to estimate the hearing capabilities of a user according to the known schemes used by otorhinolaryngologists. As a variant, the predetermined user table can comprise several measures as a function of ambient noise level.

According to one embodiment, the means for adapting the audio stream comprise several bandpass filters whose passbands are juxtaposed frequentially over the spectrum of the audio stream, the number of bandpass filters corresponding to the number of characteristic frequencies and the gain of the bandpass filters being tailored as a function of the hearing capabilities of the user. This embodiment allows the audio stream to be adapted simply and rapidly.

According to one embodiment, the system comprises means of autodiagnosis of the hearing capabilities of the user from a connected appliance by means of the user listening, for each characteristic frequency, to a sinusoidal signal whose frequency is equal to the characteristic frequency and the evolution of whose gain makes it possible to determine a detection threshold below which the user is no longer able to hear the signal emitted. This embodiment makes it possible to facilitate the measurement of the user's hearing capabilities.

According to one embodiment, the measure of the hearing capabilities varies between −40 dB and +40 dB for each predetermined characteristic frequency. This embodiment limits the band of measurement of the hearing capabilities so that it is contained within the amplitude of a conventional digital audio stream of 96 dB (quantization on 16 bits).

According to one embodiment, the characteristic frequencies are 125 Hz, 250 Hz, 500 Hz, 750 Hz, 1 KHz, 1.5 KHz, 2 KHz and 3 KHz. These characteristic frequencies are those customarily measured by otorhinolaryngologists. They are known to be representative of a user's hearing capabilities.

BRIEF DESCRIPTION OF THE DRAWINGS

The invention will be better understood with the aid of the description, given hereinafter purely by way of explanation, of the embodiments of the invention, with reference to the Figures in which.

DETAILED DESCRIPTION OF THE EMBODIMENTS OF THE INVENTION

Figure 1:
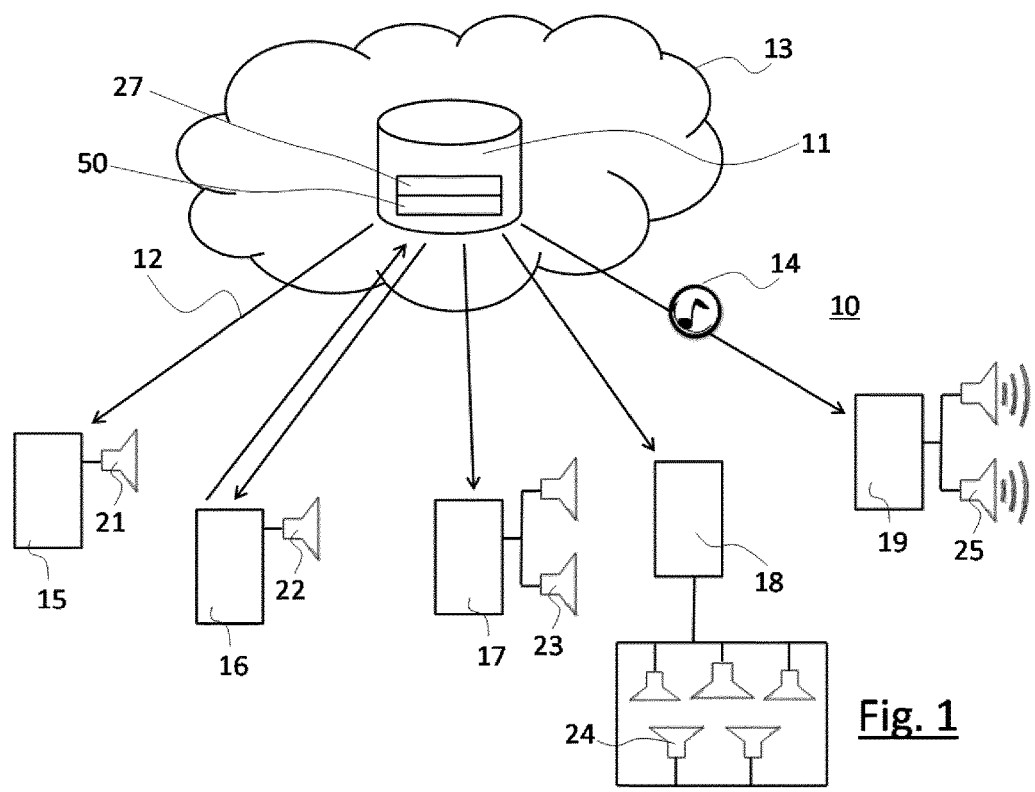
FIG. 1 illustrates a music listening optimization system according to the invention.

FIG. 1 illustrates a music listening optimization system 10 destined for several appliances 15-19 connected to a multimedia server 11. The multimedia server 11 is implanted in a so-called "Cloud" 13 and comprises means 12 for transmitting at least one audio stream 14 with the connected appliances 15-19. For example, the multimedia server 11 can stream music on an appliance connected by satellite to the Internet network. Thus, the transmission means 12 can be of any known type. The audio stream 14 is not necessarily stored on the multimedia server 11 and can be delivered by another server communicating with the multimedia server 11.

The connected appliances 15-19 can be of any known type that is able to broadcast an audio stream 14. In the example of FIG. 1, the system 10 comprises a Smartphone 15 provided with a single-channel acoustic emission means 21, a touch tablet 16 provided with a single-channel acoustic emission means 22, a connected television 17 provided with a dual-channel acoustic emission means 23, a home cinema device 18 provided with an acoustic emission means 24 of type 4.1 and a car radio 19 of a motor vehicle provided with a dual-channel acoustic emission means 25.

The multimedia server 11 comprises means 27 for selecting at least one connected appliance 15-19 and means 50 for adapting the audio stream 14 transmitted to the connected appliance 15-19 selected. In the example of FIG. 1, the selection means 27 are embodied by a control interface on which the digital tablet 16 is connected. This control interface can be embodied by an application carried on at least one connected appliance 15-19 or by a secure Internet page. In the case of FIG. 1, the touch tablet 16 and the car radio 19 being connected to the Internet, the car radio 19 is selected through the touch tablet 16 and the audio stream 14 is transmitted to the car radio 19. Preferably, the control interface makes it possible to identify the user 36-39 and to adjust certain parameters of the audio stream 14 transmitted. For example, the control interface can allow the user 36-39 to choose several predetermined different ambiences by deforming the original audio stream 20.

Figure 2:
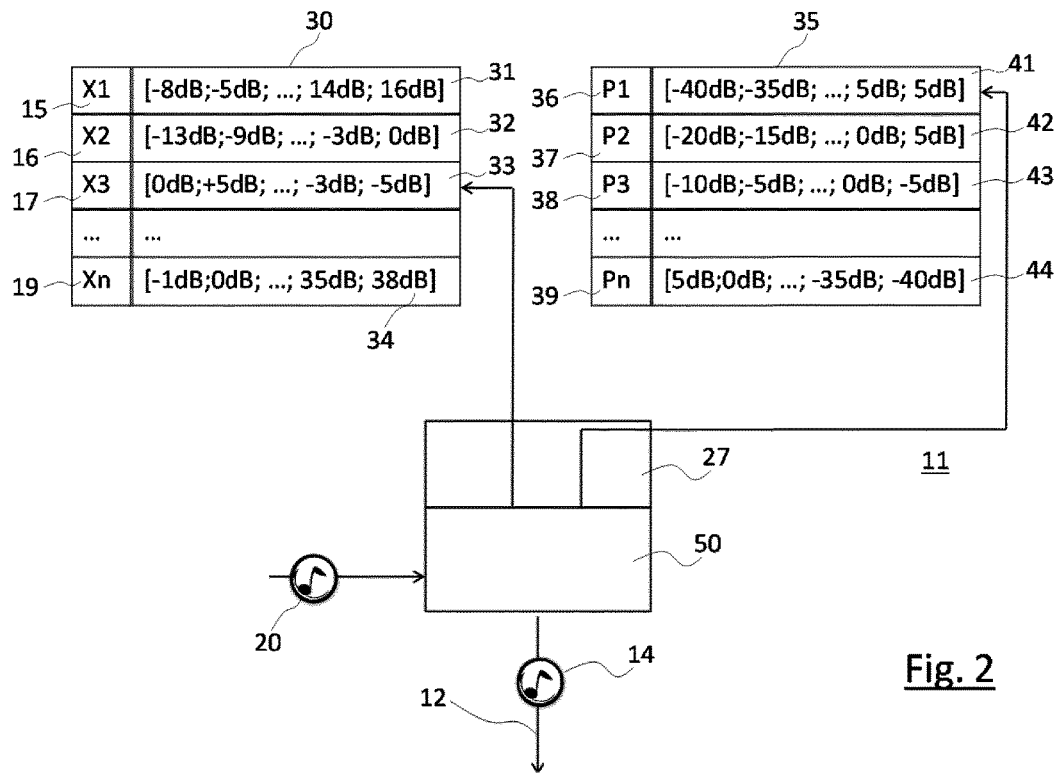
FIG. 2 illustrates the elements of the multimedia server of the optimization system of FIG. 1.

The multimedia server 11 also comprises a predetermined table of characteristics 30 and a predetermined user table 35 represented in FIG. 2. The predetermined table of characteristics 30 makes it possible to associate the various connected appliances 15-19 with a measure of their acoustic reproduction capabilities 31-34. The predetermined table of characteristics 30 is filled in during a step of installing a connected appliance 15-19 as a function of the response of the acoustic emission means 21-25 to various stimuli. Accordingly, at least one microphone is installed in proximity to the acoustic emission means 21-25. In the case of the Smartphone 15 or of the touch tablet 16, a microphone is already present on these connected appliances 15-19 and can be used. In the example of FIG. 2, the predetermined table of characteristics 30 takes the form of a vector associated with each connected appliance 15-19. This vector represents the attenuation measured at various frequencies. As a variant, the predetermined table of characteristics 30 can comprise several vectors forming a matrix, each vector of which represents the attenuation measured in a particular ambience, for example as a function of the ambient noise level.

The predetermined user table 35 is filled in during a step of defining the hearing capabilities 41-44 of a user 36-39 at several predetermined characteristic frequencies: 125 Hz, 250 Hz, 500 Hz, 750 Hz, 1 KHz, 1.5 KHz, 2 KHz and 3 KHz. Accordingly, the user 36-39 can go to an otorhinolaryngologist or carry out an autodiagnosis from a connected appliance 15-19. The measurement performed at an otorhinolaryngologist's exhibits the advantage of using calibrated measurement appliances and measurement by autodiagnosis makes it possible to perform a relative measurement by taking into account the acoustic reproduction capabilities 31-34 of the connected appliance 15-19 on which the measurement is performed. Accordingly, an application allows the user 35 to listen, for each characteristic frequency, to a sinusoidal signal whose frequency is equal to the characteristic frequency and the evolution of whose gain makes it possible to determine a detection threshold below which the user 35 is no longer able to hear the signal emitted. In the example of FIG. 2, the predetermined user table 35 takes the form of a vector associated with each user 36-39 whose values vary between −40 dB and +40 dB. This vector represents the hearing capabilities 41-44 of a user 36-39 at several predetermined characteristic frequencies. As a variant, the predetermined user table 35 can comprise several vectors forming a matrix, each vector of which represents the hearing capabilities 41-44 of a user 36-39 at several predetermined characteristic frequencies, for example as a function of the ambient noise level.

Figure 3:
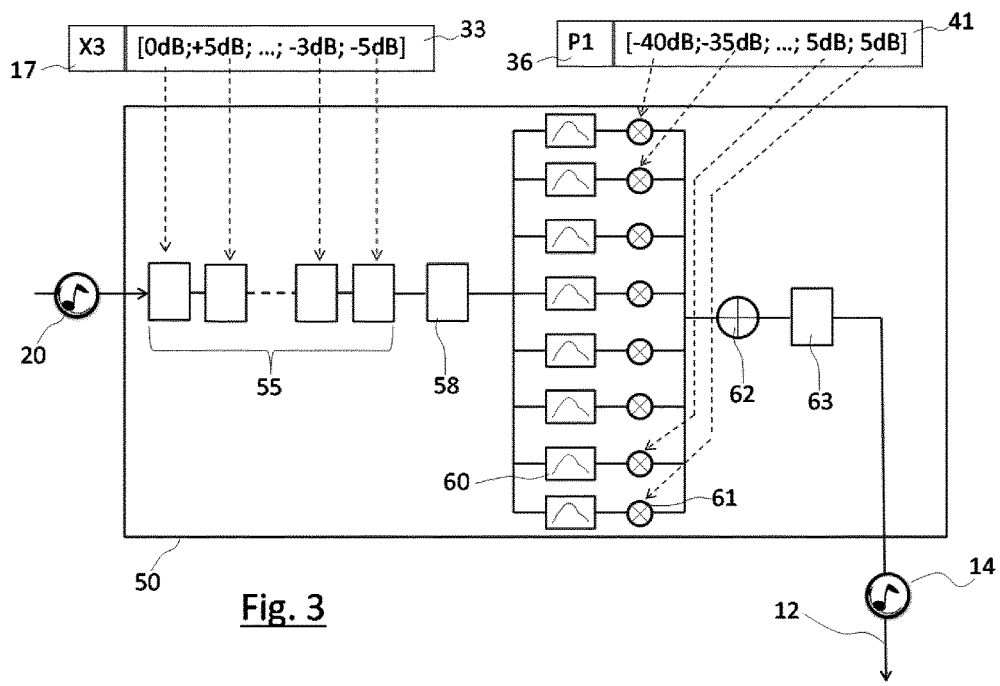
FIG. 3 illustrates the means for adapting the audio stream of the multimedia server of FIG. 2.

The means 50 for adaptation between the original audio stream 20 and the transmitted audio stream 14 are described in FIG. 3 for an exemplary embodiment. The original stream 20 is firstly adapted as a function of the connected appliance 15-19 selected and then according to the hearing capabilities 41-44 of the user 36-39.

The adaptation as a function of the connected appliance 15-19 selected is carried out by several filters of IIR ("Infinite Impulse Response") type 55 connected in series. The filters of IIR type 55 comprise characteristics of frequency, gain, order and passband type, which frequentially modify the spectrum of the audio stream 14. These characteristics are tailored as a function of the measure of the acoustic reproduction capabilities 31-34 of the connected appliance 15-19 to which said audio stream 14 is transmitted. The adaptation can be performed in an automatic manner by a dedicated algorithm or by a specialist sound engineer. When the audio stream 14 has been transformed in all the filters of IIR type 55, a normalization step 58 is performed. The normalization step 58 consists in calculating in real time the power of the audio stream 14 and in automatically compensating the volume so as to limit the saturation phenomenon.

The adaptation as a function of the hearing capabilities 41-44 of the user 36-39 is carried out by several bandpass filters 60 whose passbands are juxtaposed frequentially over the spectrum of the audio stream 14. The passband of each bandpass filter 60 is centered in a logarithmic scale on each predetermined characteristic frequency. The passband of the last bandpass filter 60 extends to half the sampling frequency of the audio stream 14. Thus, when all the passbands of the filters are added, they make it possible to retrieve the entire spectrum of the audio stream 14. The gain 56 of the bandpass filters 60 is tailored as a function of the measure of the hearing capabilities 41-44 of the user 36-39. Preferably, the gain of each bandpass filter 60 is equal to half the inverse of the measure of the hearing capabilities 41-44 of the user 36-39 but, as a variant, the ratio may be different. The signal output by each bandpass filter 60 is fed into a summator 62 to reproduce the signal as a whole and then a normalization step 63 is performed. The normalization step 63 consists in calculating in real time the power of the audio stream 14 and in automatically compensating the volume so as to limit the saturation phenomenon.

The invention thus makes it possible to optimize music listening as a function of the connected appliance 15-19 selected and of the hearing capabilities 41-44 of the user 36-39. The reproduction of the sound experienced by a given user is thus greatly improved with respect to existing devices. As a variant, other adaptations of the audio stream 14 can be performed. For example, when the audio stream emits music whose rhythmic base is calm the user may prefer to enhance listening in respect of high-pitched sounds.

Moreover, a video stream can be associated with the audio stream 14 and the system can implement means for adapting the video stream as a function of the connected appliance 15-19 or of the visual capabilities of the user 36-39. For example, the video stream can be processed by an augmentation in the colors and a reduction in the number of pixels so as to adapt to the resolution of a Smartphone.

The invention can also be implemented on automated service machines such as cash dispensers or highway toll-gates, so as to adapt the communication of the automated machine to the user. Accordingly, in the case of a cash dispenser, the chip card can contain a means for obtaining the hearing capabilities of the user of the chip card so as to adapt the instructions to the user's hearing capabilities. In the case of an automated highway toll-gate machine, a device for subscribing to the highway toll can contain the user's hearing capabilities. The invention thus makes it possible to limit the use of electronic appliances so as to improve people's hearing by transferring the auditory corrections onto the automated machines with which they are obliged to interact.

The invention claimed is:

1. A music listening optimization system comprising a multimedia server controlled by a user, said multimedia server comprising:
   a transmitter to transmit an audio stream on different connected appliances, each provided with an acoustic emitter;
   a selector to select at least one connected appliance to which said audio stream is transmitted;
   a predetermined table of characteristics linking said connected appliances with a measure of their acoustic reproduction capabilities;
   a predetermined user table linking at least one user with hearing capabilities of said at least one user;
   an adapter to adapt said audio stream as a function of the measure of the acoustic reproduction capabilities of said connected appliance to which said audio stream is transmitted and as a function of the hearing capabilities of said user connected to said multimedia server;
   wherein said predetermined table of characteristics is populated during an installation of said at least one connected appliance as a function of a response of the acoustic emitters to various stimuli;
   wherein said predetermined user table is populated while defining the hearing capabilities of said user at predetermined characteristic frequencies; and
   an auto-diagnostic tool to diagnosis the hearing capabilities of said user from said connected appliance, wherein for each predetermined characteristic frequency, a sinusoidal signal whose frequency is equal to said each predetermined characteristic frequency is transmitted to said user, and an evolution of whose gain is used to determine a detection threshold below which said user is unable to hear the sinusoidal signal.

2. The music listening optimization system as claimed in claim 1, wherein said multimedia server further comprises a transmitter to a video stream associated with said audio stream.

3. The music listening optimization system as claimed in claim 1, wherein said multimedia server further comprises a control interface usable from a connected appliance to identify said user connected to said multimedia server.

4. The music listening optimization system as claimed in claim 1, wherein the adapter comprises a plurality of filters of IIR type connected in series whose characteristics are tailored as a function of the measure of the acoustic reproduction capabilities of said connected appliance to which said audio stream is transmitted.

5. The music listening optimization system as claimed in claim 1, wherein the adapter comprises a plurality of bandpass filters whose passbands are juxtaposed frequentially over a spectrum of said audio stream, a number of bandpass filters corresponds to a number of characteristic frequencies, and a gain of each bandpass filter is tailored as a function of the hearing capabilities of said user.

6. The music listening optimization system as claimed in claim 1, wherein the measure of the hearing capabilities varies between −40 dB and +40 dB for each predetermined characteristic frequency.

7. The music listening optimization system as claimed in claim 1, wherein the predetermined characteristic frequencies are 125 Hz, 250 Hz, 500 Hz, 750 Hz, 1 KHz, 1.5 KHz, 2 KHz and 3 KHz.

* * * * *